US011298281B2

(12) United States Patent
Gadgil et al.

(10) Patent No.: US 11,298,281 B2
(45) Date of Patent: Apr. 12, 2022

(54) SYSTEM AND METHOD TO DETECT AND PREVENT NEONATE FALL FROM AN INFANT CARE DEVICE

(71) Applicant: GE Precision Healthcare LLC, Wauwatosa, WI (US)

(72) Inventors: Shruti Abhijit Gadgil, Bengaluru (IN); Nagapriya Kavoori Sethumadhavan, Bengaluru (IN); Helge B. Klockow, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 501 days.

(21) Appl. No.: 16/440,190

(22) Filed: Jun. 13, 2019

(65) Prior Publication Data

US 2020/0390628 A1    Dec. 17, 2020

(51) Int. Cl.
*A61G 11/00* (2006.01)
*A61B 5/00* (2006.01)
*A61B 5/11* (2006.01)

(52) U.S. Cl.
CPC ............ *A61G 11/00* (2013.01); *A61B 5/6892* (2013.01); *A61B 5/11* (2013.01); *A61B 2503/045* (2013.01); *A61B 2562/0252* (2013.01)

(58) Field of Classification Search
CPC .................................. A61G 11/00; A61B 5/11
See application file for complete search history.

(56) References Cited

U.S. PATENT DOCUMENTS

| | | | |
|---|---|---|---|
| 2006/0152378 A1* | 7/2006 | Lokhorst | G08B 21/22 340/666 |
| 2008/0024311 A1* | 1/2008 | Mann | A61B 5/11 340/573.1 |
| 2016/0051430 A1* | 2/2016 | Bader | A47C 31/123 128/845 |
| 2016/0069735 A1 | 3/2016 | Underwood | |
| 2018/0168903 A1 | 6/2018 | Underwood et al. | |
| 2018/0199731 A1 | 7/2018 | Starr et al. | |
| 2020/0229616 A1* | 7/2020 | Paap | A47D 13/08 |

* cited by examiner

*Primary Examiner* — John P Lacyk
(74) *Attorney, Agent, or Firm* — Andrus Intellectual Property Law, LLP

(57) ABSTRACT

An infant care device includes a mattress and mattress tray configured to support a baby and an enclosure/barrier surrounding the mattress to create a chamber around the baby. A plurality of sensors, such as load cells, are distributed beneath the mattress and mattress tray. A control unit receives information from the load cells and is able to determine the position of the baby on the mattress. A safe zone and a potential fall zone are defined in the control unit. When the determined location of the baby is within the potential fall zone, the control unit operates a resistance mechanism to restrict movement of the baby toward a perimeter edge of the mattress and generates an alarm. Multiple embodiments of the resistance mechanism are disclosed to restrict the movement of the baby.

19 Claims, 8 Drawing Sheets

SYSTEM AND METHOD TO DETECT AND PREVENT NEONATE FALL FROM AN INFANT CARE DEVICE

BACKGROUND

The present disclosure generally relates to neonatal care systems, and more specifically to neonatal care systems having a system and method to detect the location of a baby and prevent the baby from falling out of an infant care device, such as an incubator or infant warmer.

Some neonates are not physiologically well enough developed to be able to survive without special medical attention. A frequently used medical aid for such infants is the incubator. The primary objective of the incubator is to provide an environment which will maintain the neonate at a minimum metabolic state thereby permitting as rapid physiological development as possible. Neonatal incubators create a microenvironment that is thermally neutral where a neonate can develop. These incubators typically include a humidifier and a heater and associated control system that controls the humidity and temperature in the neonatal microenvironment. The humidifier comprises a device that evaporates an evaporant, such as distilled water, to increase relative humidity of air within the neonatal microenvironment. The humidifier is typically controllable such that the amount of water, or water vapor, added to the microenvironment is adjustable in order to control the humidity to a desired value. The heater may be, for example, an air heater controllable to maintain the microenvironment area to a certain temperature. Radiant heat infant warmers may be used instead of incubators for some neonates where less environmental control is required. In still other embodiments, hybrid incubator/radiant warming systems may be utilized, various embodiments of which are well known in the art.

Neonatal incubators typically define an enclosure that includes multiple portholes on the sides of the incubator that allow a nurse to contact and manipulate the baby contained within the incubator. The size and location of the portholes are designed to provide the required access to the baby while still creating a regulated environment within the enclosure. The portholes thus create openings within the enclosure which are often large enough to allow a small baby to pass therethrough. In the case of an infant warmer, the warmer includes sidewalls that can be raised and lowered by the caregiver and include latches to hold the sidewalls in the raised positions.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

The present disclosure is directed to an infant care device, such as a neonatal incubator or infant warmer, designed for use with a baby that includes an enclosure configured to create a chamber around the baby and includes a mattress tray and mattress positioned within the enclosure. The mattress includes a top support surface that supports the baby within the chamber created by the enclosure. The infant care device includes a location system that is operable to determine the location of the baby on the mattress. Based upon the determined location of the baby on the mattress, a resistance mechanism can be operated to create resistance to baby movement on the mattress and reduce the risk of the baby falling from the infant care device.

In one embodiment of the disclosure, a plurality of sensors are located beneath the mattress or the mattress tray that each generate a signal based upon a sensed weight of the baby. A control unit receives the information from the plurality of sensors and determines the location of the baby on the mattress. Based upon the determined location of the baby within either a safe zone or a potential fall zone, the control unit selectively operates the resistance mechanism to prevent further movement of the baby toward one of the edges of the mattress.

The resistance mechanism included as part of the infant care device can include one of a plurality of different mechanical devices that are each operable to restrict movement of the baby toward one of the side edges or ends of the mattress.

Various other features, objects, and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

The inventors have recognized a problem with current incubator systems for neonatal care, which is that the neonatal incubators have portholes or openings on their sidewalls so that a nurse can access the baby lying on the mattress within the incubator. The mattress can be tilted to give a head-low or head-up position. When babies are positioned within the incubator, the babies can move in all of the directions on the mattress and could potentially fall out of the portholes on the sides of the incubator, possibly resulting in life-threatening injuries. Further, a nurse may be in charge of monitoring multiple babies in multiple incubators, which decreases the amount of individual attention the nurse can give to each of the babies. In some cases, the nurse may be occupied with moving one of the babies or performing a procedure and thus is not providing full attention to the other babies under her/his care. This can be extremely challenging in stressful environments, like a neonatal intensive care unit (NICU), or where the patient-to-nurse ratio is high.

In the case of an infant warmer, the infant warmer has side walls located at each of the sides and each of the ends of the mattress that can be lowered to provide better access to the baby supported on the mattress of the infant warmer. The mattress can be tilted to give a head-low or head-up position when needed. If the side walls are not properly latched in the upright position or if one of the side walls is left in the lowered position, a risk exists that a baby could fall from the infant warmer.

Accordingly, the inventors have developed the current system that detects the position of a baby on the mattress within the infant care device, such as an incubator or warmer, utilizing sensors, such as load cells, located below the mattress or mattress tray. The system includes software and logic that identifies the location/position of the baby on the mattress and calculates the center of gravity of the baby. The system identifies if the center of gravity is within a safe zone or a potential fall zone. If the position of the baby is identified as within a potential fall zone, the system takes steps to provide resistance to further baby movement and generates an alarm about the potential fall situation so that action can be taken by the care provider to attend to this situation immediately. Various examples of mechanisms to provide resistance to movement of the baby are disclosed within the present disclosure. The disclosed system of the present disclosure may incorporate one or more systems to provide resistance to baby movement toward the outer perimeter of the mattress, such as toward one of the sides or one of the ends of the infant care device.

Figure 1:
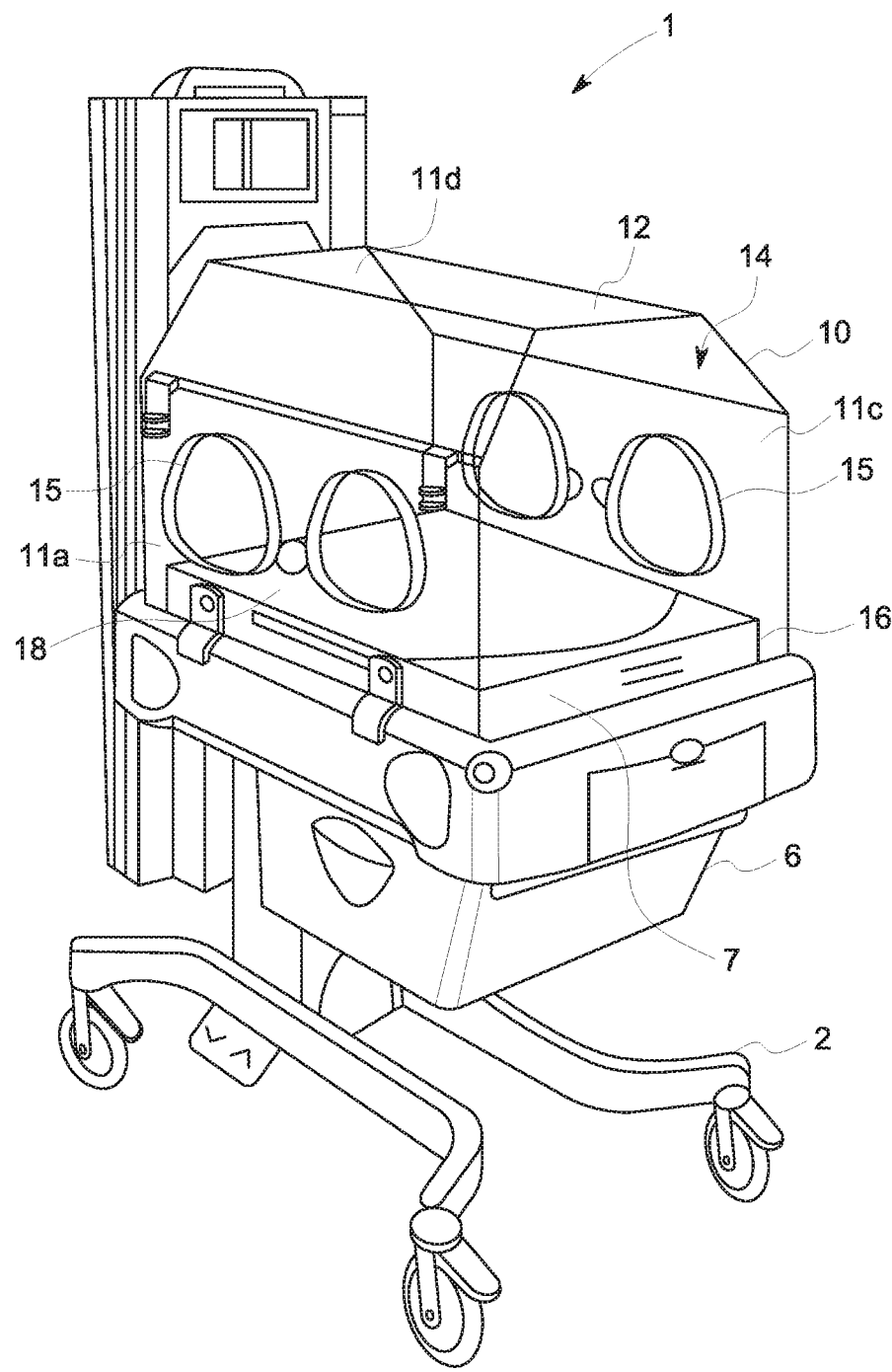
FIG. 1 is a perspective view of an exemplary neonatal incubator system in accordance with an exemplary embodiment of the present disclosure.

FIG. 1 depicts one embodiment of an infant care device having an enclosure 10. As will be understood by a person having ordinary skill in the art, the disclosed system and method may be implemented on various types of infant care devices, including incubators, incubator/warmer systems and radiant warmer systems having enclosures with side panels to create a controlled environment enclosable to secure the neonate within an area on the platform 16. The term infant care device is meant to encompass each of these different types of devices, along with other similar devices used during the care of an infant.

The depicted infant care device 1 shown in FIG. 1 is an incubator system that includes a base 2 that supports a platform 16 configured for receiving and supporting a neonate. In the depicted embodiment, the base 2 includes a horizontal section comprising a pair of u-shaped horizontal members joined together and providing support for a vertical base member extending upward toward the platform 16. The base 2 may include wheels to provide for ready movement of the incubator system 1. A platform 16 is supported on the vertical base member, which may be a standard platform for supporting a neonate, which includes a mattress tray and mattress as will be discussed below.

The incubator system 1 includes an enclosure 10 defining a chamber 14 creating a microenvironment for housing a neonate. The enclosure 10 may be, for example, a transparent housing extending above the platform 16. The enclosure 10 creates and defines a chamber 14 providing a microenvironment, which is an area around the neonate where temperature, humidity, and other environmental factors can be controlled.

Figure 2:
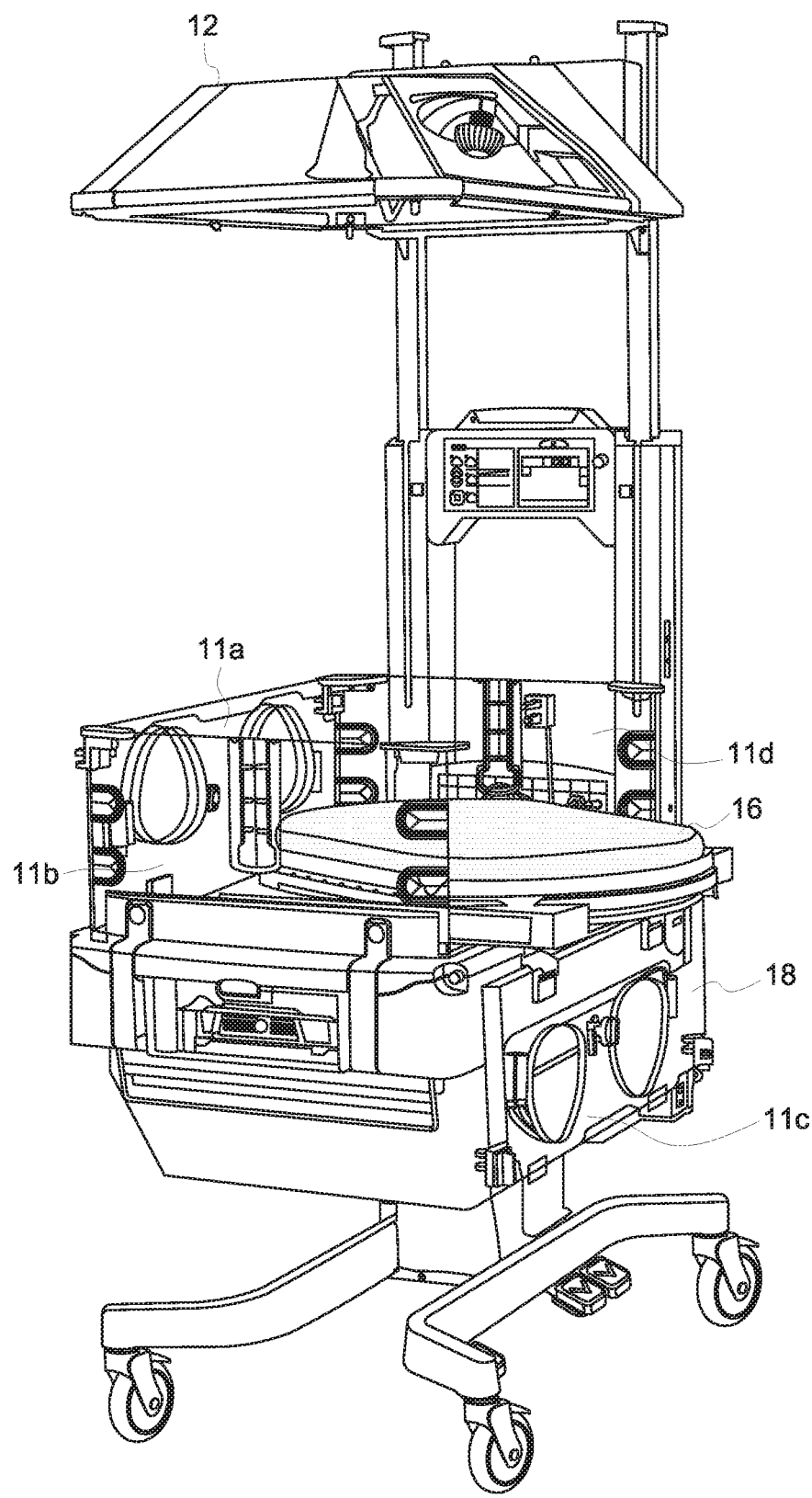
FIG. 2 depicts another embodiment of a neonatal incubator system according to another embodiment of the present disclosure.

The enclosure 10 includes multiple side walls 11a-11d and a top portion 12. For example, the side walls 11a-11d and/or the top portion 12 of the enclosure 10 may be made of a transparent plastic material, as is standard in the relevant art. In various embodiments, the top portion 12 may be integrated with the side walls 11a-11d. In other embodiments, the top portion 12 may be separable from the side walls 11a-11d of the enclosure 10, as shown in FIG. 2. In the examples, the enclosure 10 includes a plurality of portholes 15 through which a nurse may access the baby within the chamber 14. The incubator system 1 may further include a heater 7 used to control the temperature within the microenvironment of the chamber 14. For example, the chamber heater 7 may be a radiant heating or warming device that heats the air within the chamber 14 to a predefined temperature or within a predefined temperature range. In another embodiment, the heater 7 may comprise a convective or conductive heating device or any other type of controllable heating or warming device. The incubator system 1 may further include a humidifier system 6 controllable to adjust the relative humidity within with the chamber 14. For example, the humidifier may include a device that evaporates water, such as distilled water, to increase the relative humidity of air within the chamber 14.

The enclosure 10 includes one or more movable side panels 18 on a side wall 11a-11d of the enclosure 10. The movable side panel 18 is openable to place a neonate on the platform 16 enclosable to secure the neonate within the chamber 14. The movable side panel may be only part of a side wall 11a-11d of the enclosure 10, or may comprise the entirety of the side wall 11a, 11c as shown in the depicted embodiments. Although an incubator is shown in FIG. 1, an infant warmer would include similar side walls that can be raised and lowered as desired.

In FIG. 1, the movable side panel 18 is shown in a fully-closed position. FIG. 2 shows the movable side panel 18 in a fully open position. In certain embodiments exemplified at FIG. 2, the platform 16 may be configured to slide and/or rotate outward when the movable side panel 18 is open to enable easier access to a neonate and/or to enable easy placement of the baby on the platform 16.

Figure 3:
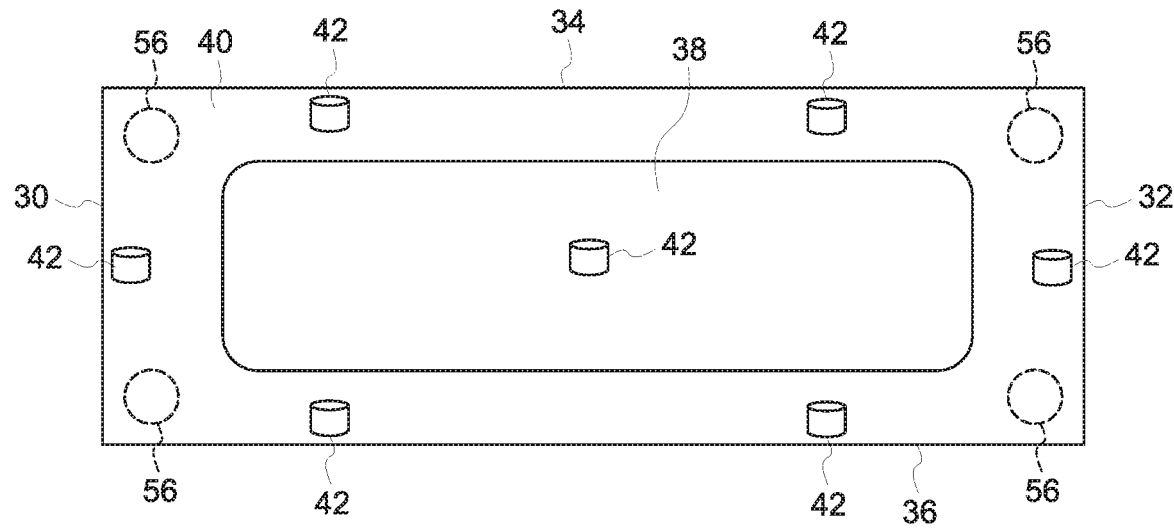
FIG. 3 depicts one exemplary embodiment of a mattress, mattress tray and multiple load cells used with an infant care device.
Figure 4:
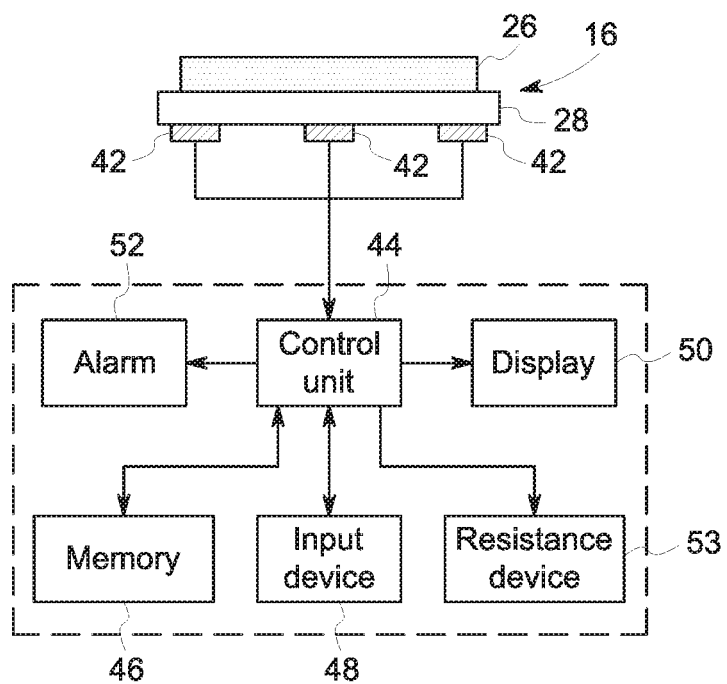
FIG. 4 is a schematic illustration of the mattress, load cells and mattress tray and the control unit in accordance with an embodiment of the present disclosure.

FIGS. 3 and 4 illustrate one embodiment of the support platform 16 constructed in accordance with the present disclosure. As illustrated in FIG. 4, the support platform 16 includes a mattress 26 resting upon a mattress tray 28. Although the mattress 26 shown in FIG. 4 is sized slightly smaller than the mattress tray 28, it should be understood that the mattress 26 could have the same size as the mattress tray 28. As can be understood in the views in FIGS. 1 and 2, the support platform 16, including both the mattress 26 and the mattress tray 28 are sized to be received within the enclosure 10 of the infant care device.

In the top view of the mattress and mattress tray shown in FIG. 3, the combination of the mattress 26 and mattress tray 28 define an outer perimeter defined by a first end 30, a second end 32, a first side 34 and a second side 36. The pair of ends and sides of the mattress and mattress tray define a support surface for a baby when the baby is positioned within the enclosure of the infant care device. In accordance with the present disclosure, a safe baby zone 38 is defined near the center of the mattress while a potential fall zone 40 surrounds the safe baby zone 38.

The potential fall zone 40 is defined as the area of the mattress between the safe baby zone 38 and the outer perimeter of the mattress defined by the first and second side edges 34, 36 and the first and second ends 30, 32. As can be understood with reference to FIG. 1, when the center of gravity of the baby is located within the potential fall zone 40, the baby is located near one of the two ends or the side walls 11A, 11C and thus near the portholes 15. Depending upon the size of the baby, the baby may be able to pass through one of the portholes 15 and potentially fall from the elevated support platform 16. When the baby is located within the safe baby zone 38 shown in FIG. 3, the baby is located a sufficient distance away from the side walls and thus the portholes 15. In the case of an infant warmer, the baby may be able to fall from one of the side edges or one of the ends if one of the side walls give way or are not properly latched. Thus, when the center of gravity of the baby is within the safe baby zone 38, there is little to no risk that the baby may fall from the infant care device. However, when the center of gravity of the baby enters into the potential fall zone 40, the risk of the baby falling from the infant care device is elevated.

As illustrated in FIG. 3, a plurality of sensors 42 can be distributed about the support area defined by the combination of the mattress and mattress tray. In the embodiment illustrated in FIG. 3, each of the sensors is a load cell that is positioned beneath the mattress tray 28, as best shown in FIG. 4. However, it is contemplated that the sensors 42 could be located between the mattress 26 and the mattress tray 28. Each of the load cells generates an electric signal based upon the amount of weight supported by the load cell. As illustrated in FIG. 3, one or more of the sensors 42 is positioned at the center of the safe baby zone 38 such that when a baby is resting on the mattress 26, the individual electric signals from the sensors 42 can be received by a control unit 44. Based on the received signals, the control unit 44 can determine where the center of gravity of the baby is located on the top surface of the mattress. Specifically, the control unit 44 can interpret the electrical signals received from the plurality of load cells to determine which load cells are generating the largest electrical signal and thus are measuring the greatest amount of weight from the baby. By interpreting the electric signals from the plurality of load cells, the control unit 44 is able to identify the approximate location of the center of gravity of the baby on the top surface of the mattress.

The control unit 44 retrieves a representation of the mattress from the memory 46. The memory 46 includes a representation of the top surface of the mattress that includes a representation of the top surface of the mattress and the locations that are defined as the safe baby zone 38 and the potential fall zone 40. Once the control unit determines the general location of the center of gravity of the baby on the mattress, the control unit compares this location to the defined safe baby zone and potential fall zone to determine whether the baby is at risk of falling from the infant care device. During the initial setup of the infant care device, the control unit can receive information about the location of the safe baby zone 38 and the potential fall zone 40 through an input device 48 or through an interactive display 50.

If the control unit 44 determines that the baby is within the potential fall zone 40, the control unit 44 can generate an alarm signal which can be shown on the display 50 or used to generate an alarm 52. The alarm 52 could be audible, visual or any other type of indicator that would alert the nurse as to a potential unsafe condition. The alarm could also be a message sent to a nurse, a nursing station or a remote location indicating that the baby is in an unsafe position and needs urgent attention from a nurse.

In addition to generating an alarm 52, the control unit 44 can control the operation of a resistance device 53 which, when activated, creates resistance to baby movement on the mattress. The resistance device 53 is a mechanical device that, when activated by the control unit 44, creates resistance to baby movement on the mattress in multiple different ways as will be described in greater detail below. Typically, the control unit 44 activates the resistance device 53 when the control unit 44 determines that the center of mass of the baby is within the potential fall zone 40.

Figure 5A:
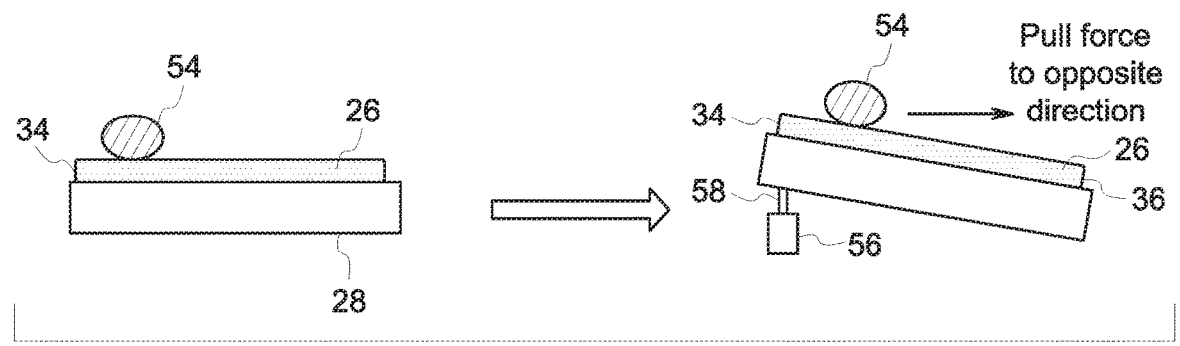
FIGS. 5A and 5B illustrate one exemplary embodiment of a system to provide resistance to movement of a baby supported within the infant care device.
Figure 5B:
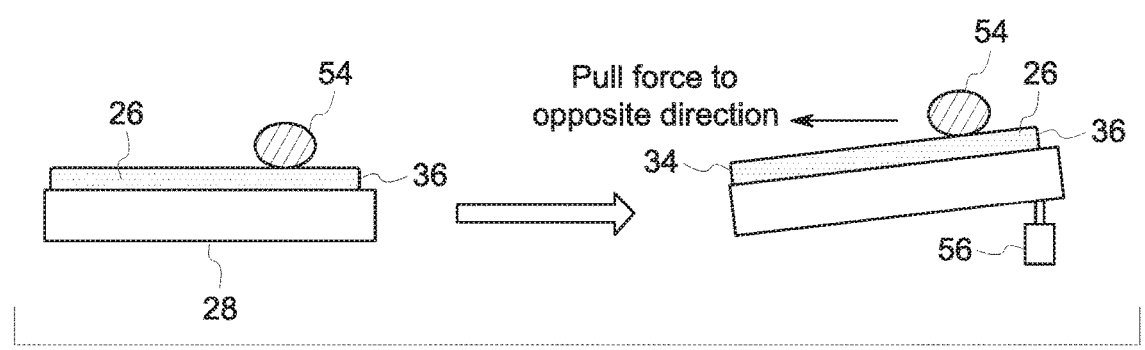

FIGS. 5A and 5B illustrate a first exemplary embodiment of a resistance mechanism that is operable by the control unit to create resistance to baby movement on the mattress. In the embodiment shown in FIG. 5A, the body mass 54 of the baby is sensed by the control unit as being close to the first side 34 of the mattress 26. In this location, the body mass 54 is within the potential fall zone 40, which causes the control unit to activate the resistance device. In the embodiment shown in FIG. 5A, the resistance device includes a pair of cylinders 56 positioned near both the first end 30 and second end 32 of the mattress tray 28 along the first side edge 34. When activated, the cylinders 56 extend a cylinder rod 58 which causes the first side edge 34 of the mattress 26 to be elevated relative to the second side edge 36. The tilting of the mattress 26 creates a pull force to resist further baby movement toward the first side edge 34 and to urge the baby toward the second side edge 36.

Although cylinders 56 are illustrated, it should be understood that a variety of different mechanisms could be utilized to raise the first side edge 34 of the mattress and mattress tray relative to the second side edge 36 of the mattress and mattress tray. For example, servo motor operated jacks, air-powered cylinders or a mechanical scissor lift could be utilized to elevate the first side edge of the mattress and mattress tray to create the tilt shown in FIG. 5A.

In the embodiment shown in FIG. 5B, the body mass 54 is sensed as being closer to the second side edge 36 of the mattress and mattress tray. Since the body mass is again in the potential fall zone, the control unit activates a pair of cylinders 56 located near the second side 36 of the mattress and mattress tray to urge the baby toward the first side 34. Once again, the cylinder 56 could be any other type of mechanism that is able to elevate the second side 36 relative to the first side 34 as illustrated in FIG. 5B.

Although not shown, a resistance device can be located near each of the two ends 30, 32 to provide resistance to the movement of the baby toward and off of either of the two ends. In each case, the resistance device would be activated when the body mass 54 of the baby moves out of the safe zone 38 and into the potential fall zone 40.

Figure 6:
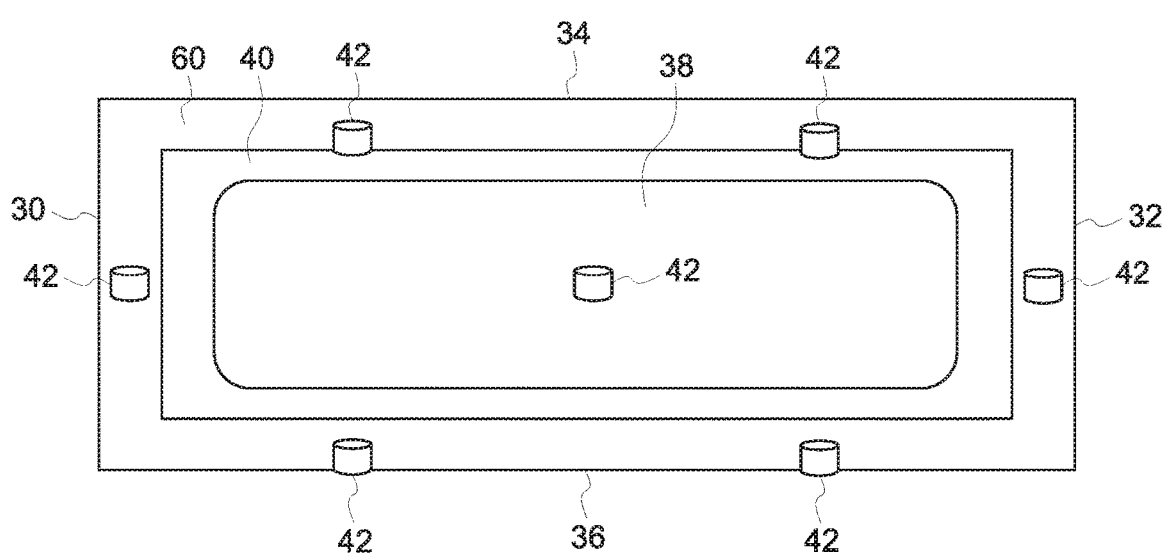
FIG. 6 depicts another exemplary embodiment of a mattress, mattress tray and load cells according to another embodiment of the present disclosure.

FIG. 6 illustrates another exemplary embodiment of a potential configuration for the mattress and mattress tray. In the embodiment shown in FIG. 6, the safe baby zone 38 is again defined near the center of the mattress and mattress tray. Surrounding the safe baby zone 38 is the potential fall zone 40. Again, a series of sensors 42, such as load cells are distributed about the entire area defined by the mattress and mattress tray. In the embodiment shown in FIG. 6, a margin area 60 is formed between the potential fall zone 40 and the first and second ends 30, 32 and first and second side edges 34, 36 of the mattress and mattress tray.

Figure 7:
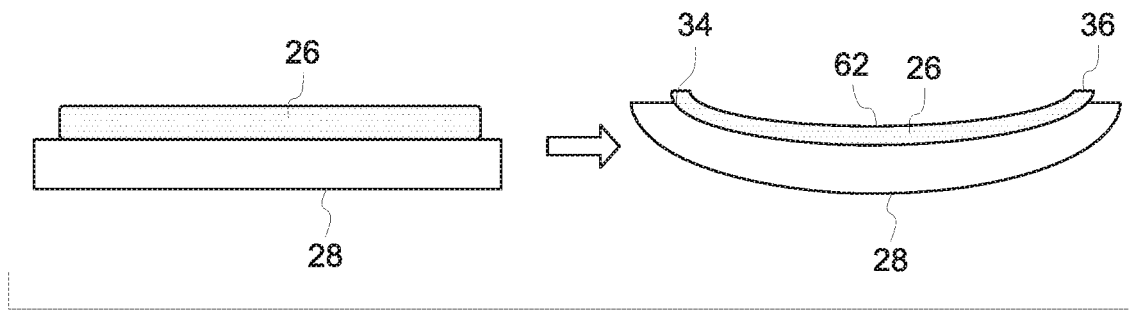
FIG. 7 illustrates another embodiment of a mattress and mattress tray to provide resistance to baby movement within the infant care device.

Another embodiment of the resistance mechanism used to create resistance to baby movement is shown in FIG. 7. In the embodiment of FIG. 7, the mattress 26 again rests upon the mattress tray 28. When the control unit determines that the center of gravity of the baby has reached the potential fall zone, the control unit activates mechanisms associated with the mattress and mattress tray to cause the mattress tray 28 to form an oval bowl shape having a concave configuration. As illustrated in FIG. 7, the mattress 26 is flexible and can conform to the shape of the mattress tray 28. In this configuration, the first side edge 34 and second side edge 36 are elevated relative to the center of the mattress and mattress tray to urge the body mass of the baby toward the center 62. It is contemplated that the mattress and mattress pad would retain this concave configuration during periods when the nurse is away from the baby, which would at all times urge the baby toward the center 62 of the mattress and mattress tray. When the nurse needs to perform a procedure or examination on the baby, the nurse could trigger the control unit to move the mattress and mattress tray to the flat configuration. However, during times when the nurse is not present, the mattress tray and mattress would return to the concave configuration to again resist movement of the baby toward either of the first or second side edges 35, 36.

Figure 8A:
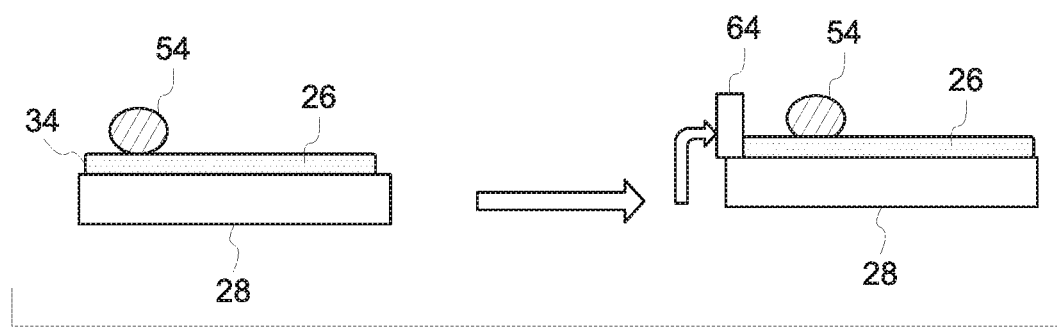
FIGS. 8A and 8B depict another embodiment of a mattress and mattress tray to provide resistance to baby movement.
Figure 8B:
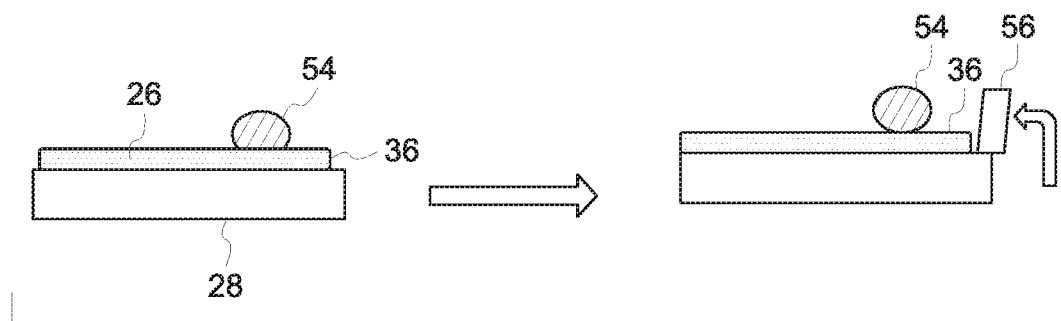

FIGS. 8A and 8B illustrate another exemplary embodiment for a mechanism that can be utilized as the resistance mechanism operated by the control unit. In the embodiment shown in FIGS. 8A and 8B, the margin area 60 shown in FIG. 6 is a portion of the mattress tray that can be raised up to 90° relative to the mattress 26 when the body mass 54 of the infant is within one of the potential fall zones. As illustrated in FIG. 8A, when the body mass 54 of the patient nears the first edge 34 of the mattress, the control unit generates a signal which causes a first edge member 64 to move to a condition in which the first edge member 64 is located at 90° relative to the mattress 26. As shown in FIG. 8A, the first edge member 64 thus creates resistance to further baby movement to prevent the baby from reaching the first side edge 34 of the mattress. Likewise, as illustrated in FIG. 8B, if the body mass 54 of the baby moves too close to the second side edge 34, a second edge member 66 is caused to move to the 90° position to prevent the baby from reaching the second side edge 36. In the embodiment shown in FIGS. 8A and 8B, both the first edge member 64 and the second edge member 66 have a width of approximately 2-4 inches to create a block or barrier to further baby movement along the mattress and to prevent the infant from reaching a wall of the incubator.

As discussed above, a resistance mechanism similar to the ones shown in FIGS. 8A and 8B can be located near one or both of the two ends 30, 32 of the mattress 26 to resist movement of the baby toward one of the ends 30 or 32. Such embodiment may be particularly useful with infant warmers that have side walls that can be lowered and in which the mattress can be tilted toward one of the ends.

Figure 9A:
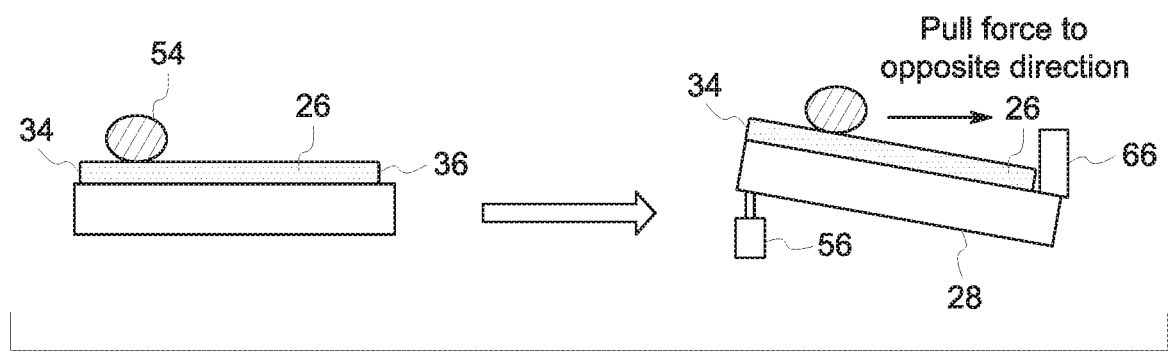
FIGS. 9A and 9B depict another embodiment of a mattress and mattress tray to provide resistance to baby movement.
Figure 9B:
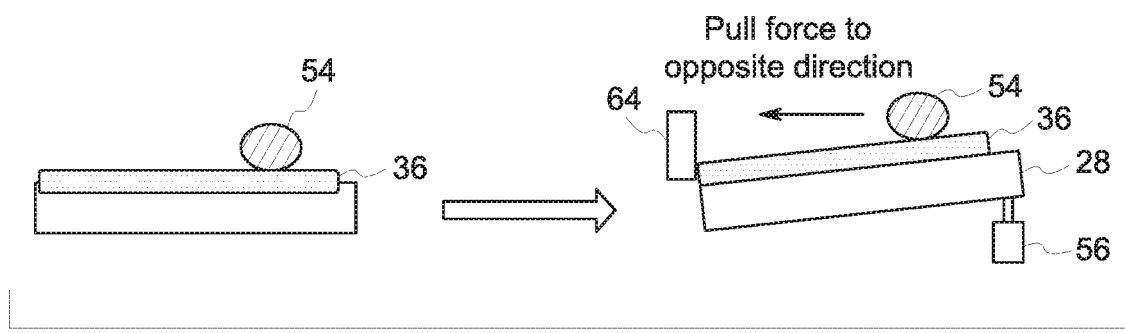

FIGS. 9A and 9B illustrate another exemplary embodiment in which the resistance mechanisms shown in FIGS. 5A and 5B are combined with the resistance mechanisms shown in FIGS. 8A and 8B. Specifically, if the body mass of the infant is sensed as being within the potential fall zone near the first side edge 34, lifting cylinders 56 are activated and the second edge member 66 is raised. In this manner, the baby is urged away from the first side edge 34 by the tilting of the mattress 26 and mattress tray 28 while the elevated second edge member 66 prevents movement of the infant too far toward the second side edge 36.

Likewise, if the infant body mass 54 is too close to the second side edge 36, the cylinders 56 near the second side edge 36 are activated and the first edge member 64 is raised. In this manner, the baby is urged toward the first side edge 34 where the first edge member 64 prevents the baby from moving too far in this direction. Thus, as can be understood in the embodiment of FIGS. 9A and 9B, more than one different type of resistance mechanism can be utilized to urge the baby from the potential fall zone and back into the safe baby zone.

Figure 10A:
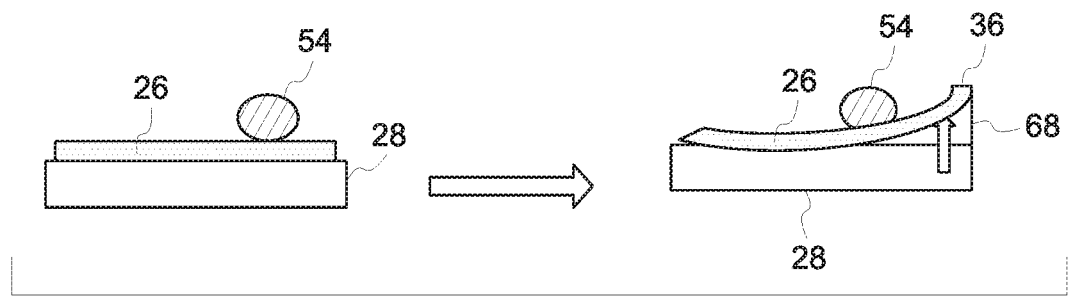
FIGS. 10A and 10B depict another embodiment of a mattress and mattress tray to provide resistance to baby movement.
Figure 10B:
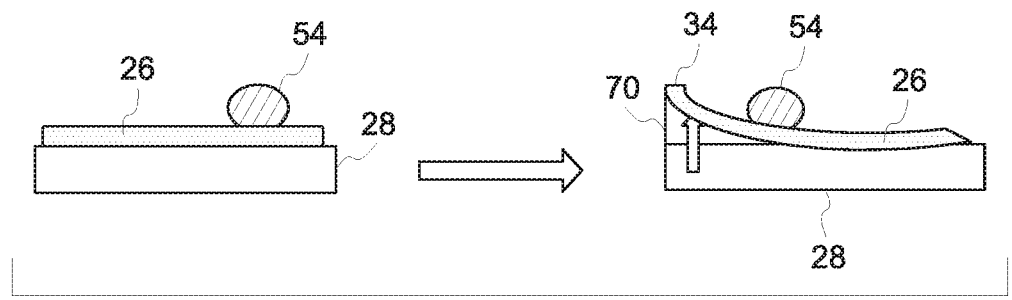

FIGS. 10A and 10B illustrate yet another exemplary embodiment of the resistance mechanism to create resistance to baby movement on the mattress 26. In the embodiment shown in FIGS. 10A and 10B, a first retractable wedge 68 and a second retractable wedge 70 are used to elevate either the first side edge 34 of the mattress 26 or the second side edge 36. As can be illustrated in FIGS. 10A and 10B, each of the first and second retractable wedges 68, 70 are extendable into and out of the mattress tray 28. When both of the retractable wedge members 68, 70 are in the retracted state, the mattress 26 is flat on the mattress tray 28. However, when the control unit determines that the center of the body mass has moved toward either the first side edge or second side edge of the mattress, the control unit can activate either the first wedge 68 or the second wedge 70 to create the resistance to baby movement as illustrated. When the baby returns to the safe baby zone, the retractable wedges 68 and 70 can again be retracted to return the mattress 26 to the flat condition illustrated. In this manner, the control unit can create a resistance to baby movement along the mattress by elevating one of the two wedge members 68 or 70. Although not shown in FIGS. 10A and 10B, additional retractable wedges can be incorporated near the first and second ends 30, 32 of the mattress tray 28 to restrict movement of the baby toward the two ends 30 and 32. The configuration of the retractable wedges near the two ends would be identical to those near the side edges and would be operated when the baby moves into the potential fall zone near one of the ends 30 or 32.

Figure 11A:
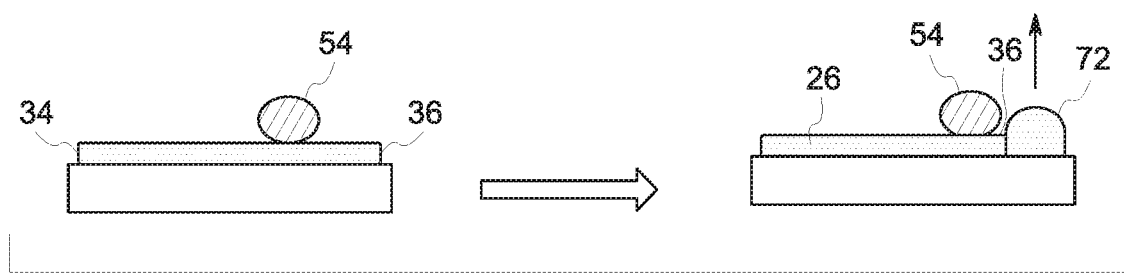
FIGS. 11A and 11B depict another embodiment of a mattress and mattress tray to provide resistance to baby movement.
Figure 11B:
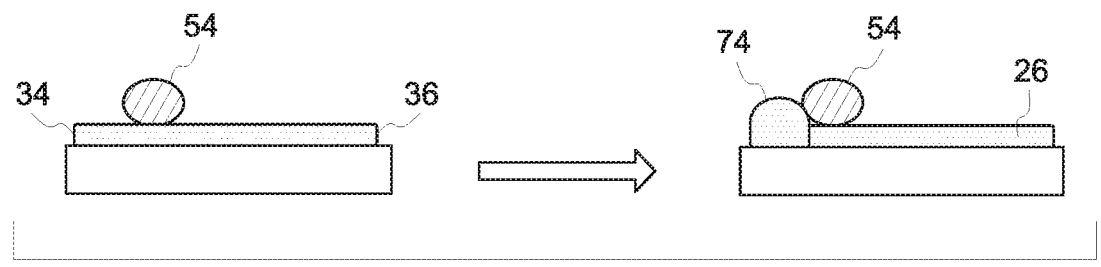

FIGS. 11A and 11B illustrate yet another exemplary embodiment of the resistance mechanism. In the embodiment shown in FIGS. 11A and 11B, a first bolster 72 is positioned near the second side edge 36 of the mattress 26 while a second bolster 74 is positioned near the first side edge 34. If the center of gravity of the baby moves toward the second side edge 36, the first bolster 72 is activated to restrict further baby movement. Likewise, if the center of gravity of the infant moves toward the first side edge 34, the second bolster 74 is activated to restrict further baby movement. In the illustrated embodiment, both the first bolster 72 and the second bolster 74 are inflatable bladders that can be inflated by the control unit to extend above the top surface of the mattress 26. The bolsters 72, 74 thus prevent further movement of the baby toward either the first side edge 34 or the second side edge 36 of the mattress. Similar bolsters can be located at or near the two ends 30, 32 of the mattress to prevent movement of the baby toward either end of the mattress.

When the body mass of the baby again moves back into the safe baby zone, the first or second bolsters 72, 74 can be deflated to return to the initial condition shown in the drawing figures. It is contemplated that the bolsters could be quickly inflated utilizing a supply of pressurized air or by utilizing an electrically operated air pump. It is contemplated that the mattress could have other types of shape changing properties that can be activated to create the resistance to movement of the baby toward the perimeter of the mattress.

Figure 12:
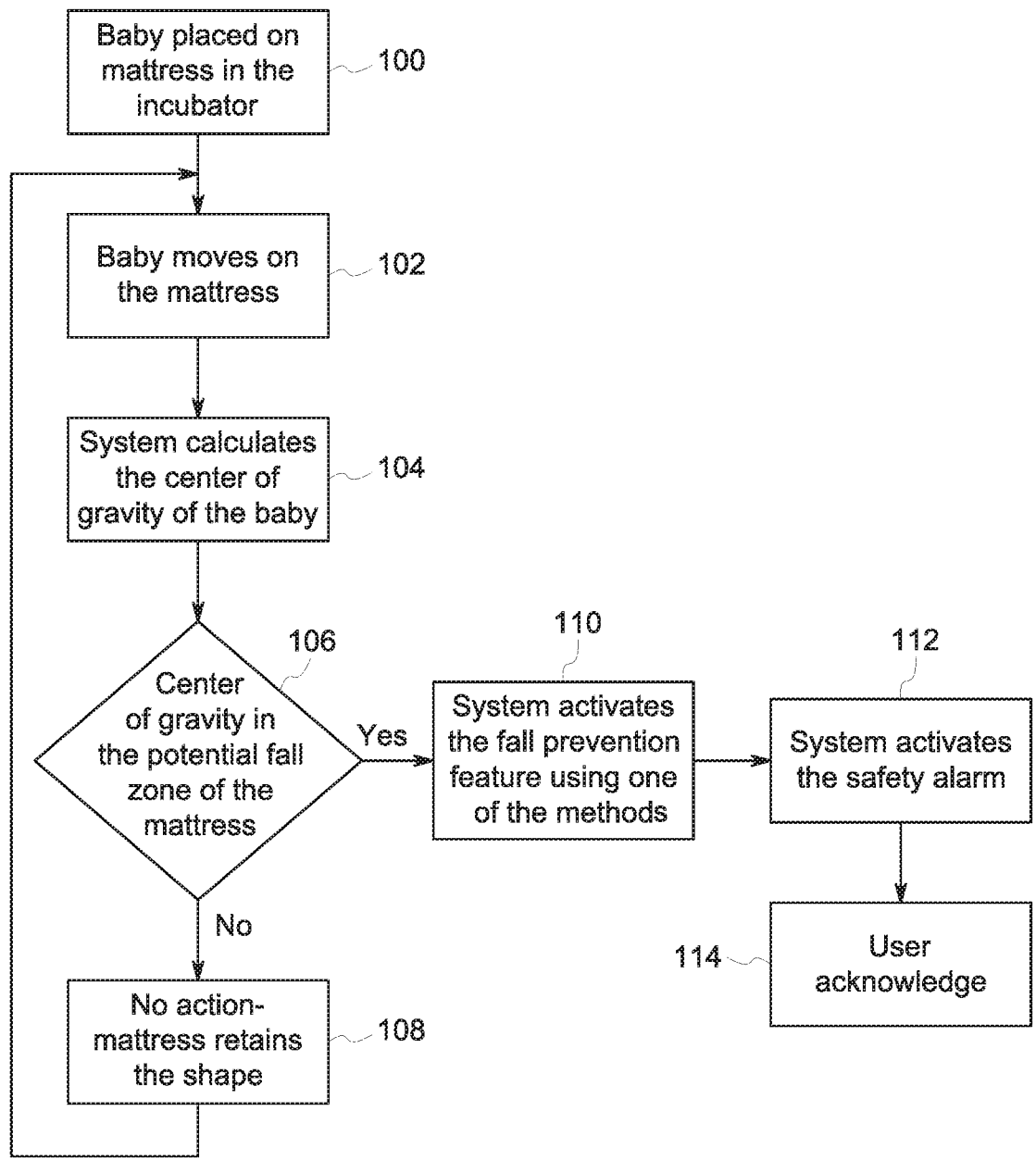
FIG. 12 depicts one exemplary embodiment of a method for sensing baby movement and providing resistance to baby movement within the infant care device.

FIG. 12 illustrates an exemplary embodiment for a method of preventing a baby from falling from an infant care device that includes a mattress supported on a mattress tray. Initially, in step 100, a baby is placed on the mattress within the infant care device. Initially, the baby is placed within the safe baby zone by a nurse. When the baby is supported on the mattress within the infant care device, the control unit 44 shown in FIG. 4 monitors the electric signals from the plurality of sensors 42. As previously described, the sensors 42 can be load cells that are positioned beneath the mattress tray, or between the mattress and the mattress tray, where each load cell generates an electric signal that is proportional to the amount of weight sensed by the individual load cell.

If the control unit 44 senses that the baby is moving on the mattress based upon changing electrical signals from the sensors 42, the system moves to step 102 where the control unit 44 obtains the electric signals from the sensors 42.

Based upon the magnitude of the signals from the load cell sensors, the control unit calculates the center of gravity of the baby in step 104. The location of the center of gravity of the baby is compared to the known outer margins of the combination of the mattress and mattress tray. In step 106, the control unit determines whether or not the center of gravity for the baby is within the potential fall zone or whether the center of gravity is within the safe baby zone. If the center of gravity is not within the fall zone, the control unit moves to step 108 and no action is taken and the mattress retains its shape. The system then returns to step 102 where the control unit again monitors for any additional movement of the baby on the mattress.

If the system determines in step 106 that the center of gravity of the baby is within the fall zone of the mattress, the system moves to step 110 where the control unit activates one of the resistance mechanisms to provide restriction to the further movement of the baby on the mattress. As described in detail above, various different resistive force mechanisms are contemplated as being within the scope of the present disclosure. However, each resistance mechanism is designed to create resistance to baby movement on the mattress.

In addition to activating one of the resistance mechanisms, the control unit activates a safety alarm in step 112. The safety alarm can be one of a variety of different alarm types, such as an audible alarm, a visual alarm, and indicator on a remote monitoring display or a message sent to a nurse, or a combination of any one of these techniques.

The control unit continues to activate the safety alarm and the resistance mechanism until the user acknowledges the alarm and moves the baby as illustrated in step 114. Once the baby has been moved and the alarm acknowledged, the system returns back to step 102 and monitors for additional movement of the baby on the mattress. In this manner, the control unit is able to monitor the baby location on the mattress and activate resistance mechanisms to restrict additional baby movement while also alerting a nurse as to the potentially dangerous location of the baby along the mattress.

In the embodiment shown in the drawing figures, the sensors 42 are described and shown as being load cells that are positioned beneath the mattress tray 28 and are connected to the control unit such that the control unit can detect and determine the location of the center of gravity for the baby. Although load cells are contemplated as being one exemplary embodiment, it is contemplated that other types of sensors could be utilized while operating within the scope of the present disclosure.

As an illustrative example, a grid of thermal sensors could be created as part of a blanket positioned over the mattress or as part of the mattress itself. The grid of thermal sensors would create either a coarse or a fine grid based upon the desired accuracy and the proximity required. Each of the individual thermal sensors would generate an electric signal to the control unit and the control unit could sense the location of the baby relative to the grid of sensors. The thermal sensors in contact with the patient or positioned below the patient would return a temperature higher than the internal temperature within the environment created within the enclosure and the control unit could thus sense and determine the position of the baby on the mattress. As with the embodiment that utilized the load cells, when the control unit senses a change in the output signals from the thermal sensors, such change would indicate movement of the baby on the mattress. Once the movement of the baby is detected, such as in step 102 of FIG. 8, the system determines whether the baby is in a potential fall zone and performs similar functions to limit further movement of the baby on the mattress.

In addition to sensing the location of the baby, the grid of thermal sensors can also be used to monitor the environment within the enclosure defined by the incubator when a patient is not present. Since the thermal sensors are laid out in a grid over the mattress, the thermal sensors provide an accurate and distributed measurement of the temperature within the infant care device.

As discussed above, the inventors have recognized a problem with existing infant care devices, including incubators, incubator/warmer systems and infant warmers, where the sidewalls of the enclosure may be lowered or not properly latched or where the size of the portholes 15 may allow a small, premature baby to pass through the portholes 15 and fall from the platform 16. Accordingly, the inventors have developed a solution that monitors the location of the baby on the platform 16 and generates an alarm when the baby moves outside of a safe zone and activates one of multiple different types of mechanisms to provide resistance to additional movement of the baby within the enclosure of the infant care device.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An infant care device for use with a baby, comprising:
 a mattress tray;
 a mattress positioned on the mattress tray and configured to support the baby within the infant care device;
 a location system operable to determine the location of the baby on the mattress; and a resistance mechanism operable to create resistance to baby movement on the mattress, wherein the resistance mechanism is operated based on the determined location of the baby on the mattress.

2. The infant care device of claim 1 wherein the location system comprises:
a plurality of sensors located beneath the mattress or mattress tray; and
a control unit that receives information from the plurality of sensors,
wherein the control unit is operable to determine the location of the baby on the mattress based on the information from the plurality of sensors.

3. The infant care device of claim 2 wherein mattress includes a perimeter edge and the plurality of sensors are a plurality of load cells distributed near the perimeter edge of the mattress and beneath a center of the mattress.

4. The infant care device of claim 3 wherein the control unit defines a safe zone and a potential fall zone for the mattress and operates the resistance mechanism when the baby is located within the potential fall zone.

5. The infant care device of claim 1 wherein the mattress and mattress tray have a first side edge, a second side edge, a first end and a second end, wherein the resistance mechanism is operable to tilt the mattress and mattress tray toward either the first side edge or the second side edge or toward either of the first end or the second end based on the determined location of the baby on the mattress.

6. The infant care device of claim 5 wherein the resistance mechanism is operable to elevate the first side edge, the second side edge, the first end or the second end of the mattress and mattress tray.

7. The infant care device of claim 1 wherein the mattress and mattress tray have a first side edge and a second side edge, wherein the resistance mechanism is operable to elevate both the first side edge or the second side edge of the mattress and mattress tray based on the determined location of the baby on the mattress.

8. The infant care device of claim 1 wherein the mattress and mattress tray have a first side edge, a second side edge, a first end and a second end, wherein the resistance mechanism is operable to elevate the first side edge, the second side edge, the first end or the second end of the mattress tray based on the determined location of the baby on the mattress.

9. The infant care device of claim 1 wherein the mattress and mattress tray have a first side edge, a second side edge and a first end, wherein the resistance mechanism includes a first wedge recessed into the first side edge of the mattress tray, a second wedge recessed into the second side edge of the mattress tray and a third wedge recessed into the first end, wherein the first, second and third wedges can be extended to restrict movement of the baby based on the determined location of the baby on the mattress.

10. The infant care device of claim 1 wherein the resistance mechanism includes inflatable bolster located along a perimeter edge of the mattress tray, wherein the inflatable bolster can be inflated to extend above at least a portion of the perimeter edge of the mattress tray based on the determined location of the baby on the mattress.

11. An infant care device for use with a baby, comprising:
a mattress tray;
a mattress positioned on the mattress tray and configured to support the baby;
a plurality of sensors located beneath the mattress or mattress tray;
a control unit that receives information from the plurality of sensors; and
a resistance mechanism operable to create resistance to baby movement on the mattress,
wherein the control unit is operable to determine the location of the baby on the mattress based on the information from the plurality of sensors and to operate the resistance mechanism to create resistance to baby movement on the mattress.

12. The infant care device of claim 11 wherein the plurality of sensors are a plurality of load cells distributed beneath the mattress near the perimeter edge of the mattress and beneath a center of the mattress.

13. The infant care device of claim 12 wherein the control unit defines a safe zone and a potential fall zone for the mattress and operates the resistance mechanism when a center of gravity of the baby is located within the potential fall zone.

14. The infant care device of claim 13 wherein the control unit generates an alarm when the baby is located within the potential fall zone.

15. A method of preventing a baby from falling from an infant care device including a mattress supported on a mattress tray, comprising:
positioning a plurality of sensors beneath the mattress or the mattress tray;
determining a location of the baby on the mattress based on information received from the plurality of sensors; and
activating a resistance mechanism to restrict movement of the baby based on the determined position of the baby on the mattress.

16. The method of claim 15 wherein the plurality of sensors are in communication with a control unit and wherein the control unit controls the activation of the resistance mechanism.

17. The method of claim 16 wherein the control unit defines a safe zone and a potential fall zone for the mattress and operates the resistance mechanism when the baby is located within the potential fall zone.

18. The method of claim 17 wherein the control unit generates an alarm when the baby is located within the potential fall zone.

19. The method of claim 15 wherein the plurality of sensors are a plurality of load cells distributed beneath the mattress near the perimeter edge of the mattress and beneath a center of the mattress.

* * * * *